(12) United States Patent
Kremer et al.

(10) Patent No.: US 9,095,397 B2
(45) Date of Patent: Aug. 4, 2015

(54) ARRANGEMENT FOR INSERTION OF IMPLANTS

(75) Inventors: Egbert Kremer, Hanau (DE); Volker Biehl, Neunkirchen (DE); Andre Spanel, Neustadt a.d. Weinstrasse (DE); Philip Cantzler, Mannheim (DE)

(73) Assignee: Friadent GmbH, Mannheim (DE)

( * ) Notice: Subject to any disclaimer, the term of this patent is extended or adjusted under 35 U.S.C. 154(b) by 640 days.

(21) Appl. No.: 12/448,188

(22) PCT Filed: Dec. 10, 2007

(86) PCT No.: PCT/EP2007/010741
§ 371 (c)(1),
(2), (4) Date: Feb. 16, 2010

(87) PCT Pub. No.: WO2008/071368
PCT Pub. Date: Jun. 19, 2008

(65) Prior Publication Data
US 2010/0248181 A1    Sep. 30, 2010

(30) Foreign Application Priority Data
Dec. 14, 2006   (DE) .................... 20 2006 020 210 U

(51) Int. Cl.
*A61C 3/00*    (2006.01)
*A61C 8/00*    (2006.01)
(Continued)

(52) U.S. Cl.
CPC ............. *A61C 8/0089* (2013.01); *A61B 17/888* (2013.01); *A61B 17/861* (2013.01); *A61B 17/8615* (2013.01)

(58) Field of Classification Search
CPC .... A61C 8/009; A61C 8/0089; A61C 8/0066; A61B 17/888; A61B 17/861; A61B 17/8615

USPC .................. 433/141, 172–176, 152
See application file for complete search history.

(56) References Cited

U.S. PATENT DOCUMENTS

| 4,824,372 A | * | 4/1989 | Jorneus et al. ................ 433/174 |
| 5,129,823 A | * | 7/1992 | Hughes ......................... 433/141 |

(Continued)

FOREIGN PATENT DOCUMENTS

| DE | 94 17 182.3 | 12/1994 |
| DE | 101 29 684 | 1/2003 |

(Continued)

OTHER PUBLICATIONS

Engish language translation WO 2006/082050, published Aug. 10, 2006.*

*Primary Examiner* — Heidi M Eide
(74) *Attorney, Agent, or Firm* — Jordan and Hamburg LLP

(57) ABSTRACT

The invention relates to an arrangement for insertion of an implant, in particular of a dental implant, which has an external thread and can be screwed into a bone by means of a tool, wherein the implant has a receiving opening with an at least partially conical inner face. A pin of an attachment part, which can be connected to the implant after the latter's insertion, can be fitted into the receiving opening. The arrangement is to be further developed such that the insertion of the implant can be performed in a simple and yet functionally reliable manner. For this purpose, it is proposed that a screwing-in tool has a pin with a conical outer face, which pin engages in the receiving opening of the implant, and that the conical outer face is designed corresponding to the conical inner face of the implant, and bears at least partially thereon, such that at least a predetermined part of the torque necessary for screwing in the implant can be transmitted via the self-inhibiting cone connection of the screwing-in tool with the implant.

19 Claims, 4 Drawing Sheets

(51) Int. Cl.
  *A61B 17/88* (2006.01)
  *A61B 17/86* (2006.01)

(56) References Cited

U.S. PATENT DOCUMENTS

| | | | |
|---|---|---|---|
| 5,437,550 A * | 8/1995 | Beaty et al. | 433/141 |
| 5,674,072 A | 10/1997 | Moser et al. | |
| 5,727,942 A * | 3/1998 | Hartmann et al. | 433/173 |
| 5,733,124 A * | 3/1998 | Kwan | 433/173 |
| 5,782,918 A | 7/1998 | Klardie et al. | |
| 5,879,161 A * | 3/1999 | Lazzara | 433/173 |
| 5,944,525 A * | 8/1999 | Ura | 433/173 |
| 6,068,480 A * | 5/2000 | Misch et al. | 433/173 |
| 6,086,371 A * | 7/2000 | Bassett et al. | 433/173 |
| 6,102,702 A * | 8/2000 | Folsom et al. | 433/172 |
| 6,261,097 B1 * | 7/2001 | Schmutz et al. | 433/173 |
| 6,280,192 B1 | 8/2001 | Groll et al. | |
| 6,312,260 B1 * | 11/2001 | Kumar et al. | 433/174 |
| 6,447,295 B1 * | 9/2002 | Kumar et al. | 433/172 |
| 6,648,643 B2 * | 11/2003 | Hollander et al. | 433/173 |
| 6,663,388 B1 | 12/2003 | Schaer et al. | |
| 7,090,495 B1 * | 8/2006 | Rosen | 433/174 |
| 7,160,109 B2 * | 1/2007 | Gervais et al. | 433/141 |
| 7,309,231 B2 * | 12/2007 | Engman | 433/173 |
| 8,202,088 B2 * | 6/2012 | Mehrhof | 433/173 |
| 2002/0127516 A1 * | 9/2002 | Lang et al. | 433/173 |
| 2004/0175673 A1 | 9/2004 | Zickman et al. | |
| 2005/0186537 A1 * | 8/2005 | Gersberg | 433/173 |
| 2006/0105296 A1 * | 5/2006 | Linder et al. | 433/173 |
| 2006/0217738 A1 | 9/2006 | Tanimura | |
| 2006/0286508 A1 * | 12/2006 | Bassett et al. | 433/172 |
| 2007/0037123 A1 * | 2/2007 | Mansueto et al. | 433/173 |
| 2007/0117066 A1 * | 5/2007 | Jorneus et al. | 433/173 |
| 2008/0182227 A1 | 7/2008 | Wolf et al. | |

FOREIGN PATENT DOCUMENTS

| | | | |
|---|---|---|---|
| DE | 10 2005 005 402 | 8/2006 | |
| DE | 10 2006 059 515 | 8/2007 | |
| EP | 0 707 835 | 4/1996 | |
| FR | 2 853 828 | 10/2004 | |
| WO | WO 2005030081 A1 * | 4/2005 | |
| WO | WO-2006/012273 | 2/2006 | |
| WO | WO 2006082050 A1 * | 8/2006 | A61C 8/00 |
| WO | WO-2008/022635 | 2/2008 | |

\* cited by examiner

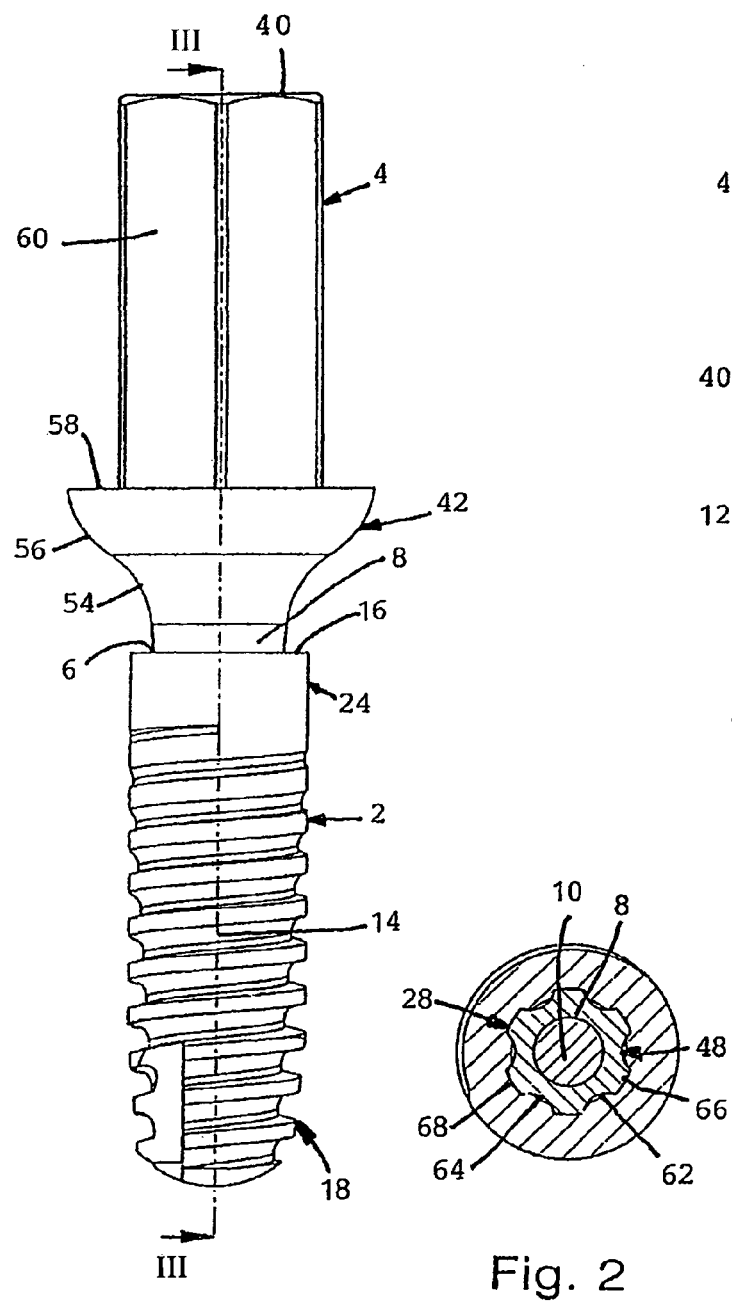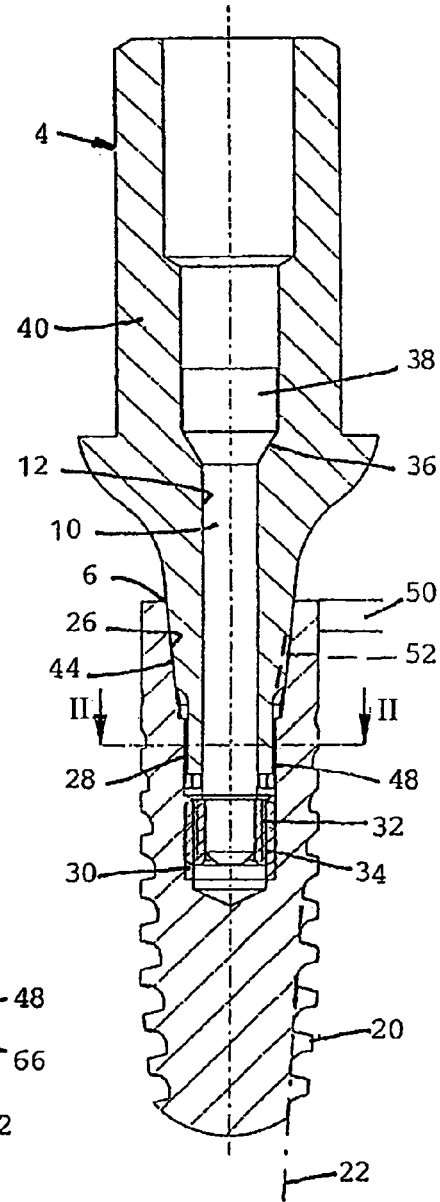
Fig. 1
Fig. 2
Fig. 3

ARRANGEMENT FOR INSERTION OF IMPLANTS

BACKGROUND OF THE INVENTION

The invention relates to an arrangement for insertion of implants, in particular dental implants.

Such an arrangement having an implant with a male thread is known from DE 94 17 182 U1. The implant is embodied as a dental implant and includes a receiving opening that extends apically from the coronal end area and that is for a pin of an attachment part that can be connected to the implant after it has been inserted into a bone, in particular a jaw bone. The receiving opening includes a conical interior surface that opens towards the coronal end and apically adjacent a first indexing element in the form of a polygonal receiving element and a threaded bore. Analogously, the pin of the attachment part includes a conical exterior surface and a second indexing element in the form of a polygonal element that can be inserted into the polygonal receiving element in the implant. Provided for connecting the attachment part to the implant is a tension or retaining screw that passes through a through-hole in the attachment part and can be screwed into the threaded bore of the implant by means of a male thread. Provided for inserting the implant into the bone is a tool having a polygonal element that conforms to the polygonal receiving element in the implant and can be inserted therein. The torque for inserting the implant is transferred only via the polygonal receiving element and consequently during insertion or screwing-in there is a risk that the polygonal receiving element of the implant that is embodied as the indexing element will be damaged and thus the proper connection of the attachment part to the implant, and above all the exact orientation of the attachment part with respect to the implant in a pre-defined rotational angle position, is called into question. The first indexing element is disposed in an area in which the implant does not have any external thread. The male thread is arranged spaced apart from the indexing element in the axial direction, and it extends approximately from the center of the longitudinal extension of the implant to its apical end. Since the aforesaid indexing element is then provided axially adjacent to the conical interior surface of the implant, the conical interior surface of the implant body extends only across a portion of its entire length so that for the conical connection to the attachment part only a very small or axially short connecting surface is available, there being a comparatively large takeout angle for the aforesaid conical surfaces.

Furthermore, known from EP 0 707 835 B1 is a dental implant with a central receiving opening that has a conical interior surface that opens toward the coronal end and in the interior end region has a female thread for anchoring a tension screw. It is possible to insert into the receiving opening a pin of an attachment part, the tension screw passing through the through-hole thereof, the through-hole being provided, in a head area of the attachment part that faces the oral cavity, an extension for receiving a head of the tension screw. The aforesaid pin of the attachment part includes an exterior surface that conforms to the conical interior surface of the receiving opening. The conical interior surface of the receiving opening and the conical exterior surface of the pin are embodied such that there is a self-locking conical connection between the implant and the attachment part connected by means of the tension screw. This form-fit and press-fit conical connection provides the attachment part continuous anti-rotational resistance against the high loads with regard to the implant. For placing the implant in the jawbone, the implant has, in its coronal region or the coronal end surface, engaging elements for a tool, such as for instance slits that open in the occlusal direction for a screwdriver. The attachment part can be positioned in a stepless manner relative to the implant in terms of the longitudinal axis in any desired rotational angle position, special measures for conforming transfer or orientation of the attachment part with respect to the implant being necessary in particular in the dental laboratory and/or when the impression is taken that is necessary for preparing a superstructure.

Moreover, known from DE 10 2005 005 402 A1 is a dental implant containing an implant body having a central receiving opening, an attachment part that has a pin that engages in the aforesaid receiving opening, and a tension screw that passes through a through-hole in the attachment part and that after the implant body has been inserted is screwed into a female thread in the receiving opening. So that it can be inserted in a jawbone, the implant body has placement elements in the region of its coronal end, whereby the screwing tool can be embodied for instance as a screwdriver and the placement elements can be embodied as slits for the tool that can engage with them. After the implant body has been inserted, the attachment part is connected to it, the rotational position of the attachment being determined relative to the implant body by means of indexing elements that are provided in the receiving opening of the implant body and on the pin of the attachment part.

SUMMARY OF THE INVENTION

The underlying object of the invention is to further refine a dental implant such that the implant can be inserted in a simple manner that also assures function. It should be simple to produce the arrangement and it should also be possible to employ the arrangement even for very small filigree implants, such as for instance so-called mini-implants. Reliable insertion should be possible while damage to the indexing element is prevented. Moreover, the indexing should be very precise and/or damages and/or overloads should be prevented.

The proposed arrangement is distinguished by a functionally appropriate design, the torque being at least partially transmitted via the self-locking conical connection between the screwing tool and the implant during insertion thereof. The exterior conical surface of the pin that engages in the receiving opening and the conical interior surface of the implant conform to one another such that a pre-defined portion of the torque to be introduced is transferred via the adjacent conical surfaces of the screwing tool and the implant onto the implant. Usefully, only a pre-definable partial region of the entire conical interior surface of the implant is used for transferring torque. This partial region is advantageously provided in the part of the conical interior surface that is adjacent to the coronal end of the implant. To this end, the takeout angle for the conical exterior surface of the screwing tool is slightly larger than the takeout angle of the conical interior surface of the implant, specifically such that at the aforesaid partial region the aforesaid conical surfaces in the apical direction are practically no longer adjacent to one another and/or do not contribute to transferring torque. Alternatively, the conical part of the pin, if the latter engages in the receiving opening, can be shorter than the total length of the conical interior surface, the takeout angles of the adjacent conical surfaces being essentially identical. Finally, in accordance with the invention the takeout angle of the conical exterior surface of the screwing tool can be slightly smaller than the takeout angle of the conical interior surface so that the partial region of the support is preferably spaced apart from the coronal end surface of the implant. Thus there is a pre-definable or adjustable portion of the torque transmission provided by varying the clamping surface in the aforesaid partial region or its size, the remainder of the conical interior surface of the implant remaining free or unclamped with the screwing tool or its exterior conical surface. The remainder of the torque to be applied is usefully absorbed by other elements, in particular by means of mutually engaging indexing elements for the screwing tool and the implant or by means of jamming or running up a corresponding stop face for the screwing tool on the upper edge or coronal end surface of the implant or by means of jamming or clamping the screwing tool with the implant by means of a screw thread.

The screwing tool is connected to the implant at the plant and/or pre-tensioned in a defined manner, specifically by means of a tension screw that passes through a through-hole in the screwing tool and that with a thread is screwed into a female thread arranged in the receiving opening of the implant. The screwing tool is advantageously pre-mounted with the implant and/or embodied as a screw-in post and contains a head part provided outside of the implant for a different tool or instrument, such as elbow or ratchet brace. Moreover, the screwing tool can be embodied as a separate instrument for an elbow or when designed as a pre-mounted screw-in post with elbow connector. The head part of the screwing tool advantageously possesses at least one gripping surface for the appropriate tool or instrument, such as ratchet or the like. Moreover, the head part can be embodied in a preferred manner for a temporary structure, such as a crown, or can be used as such.

Due to the inventive embodiment and arrangement of the screwing tool combined with the implant and/or the at least partial transferability of the torque via the self-locking conical connection between the screwing tool and the implant, there is great certainty that the highly precise indexing element of the latter will not be damaged when it is screwed in. The indexing element can thus be embodied in a relatively space-saving manner, i.e. with limited structural volume, whereby it is useful that it is possible to prevent damage resulting from overloading. This is of particular significance given that the implant sizes and/or shapes are growing increasingly smaller and more filigreed. Due to the use of the conical clamping between the screwing tool and the implant, the indexing element is reliably protected, it being possible to match or divide the portion of torque to be transferred via the conical or clamping surfaces with no problem. The precision for the anti-rotation assurance of the attachment part to be connected to the implant after insertion is provided with great reliability since the indexing element for the implant is not damaged during insertion. It is noted here that the rotational forces acting via the attachment part and/or prosthetic are significantly less than the torque to be introduced onto the implant when it is inserted. Furthermore, it should be expressly noted that the arrangement in the framework of the invention includes implants with or without indexing elements and furthermore the screwing tool has corresponding indexing elements or does not have them. If the screwing tool has indexing elements, the latter can preferably be embodied and/or arranged such that the screwing tool can be used and/or caused to engage with implants that have indexing elements or contain no indexing elements.

Since inventively only a partial region of the conical interior surface of the implant is used for transferring torque, undesired "seizing up" of the screwing tool or its conical exterior surface relative to the implant is avoided in a particularly useful manner and thus after the implant has been inserted the necessary release and removal of the screwing tool from the implant is assured with no problem. Moreover, it has proved particularly useful to pre-tension the screwing tool with the implant at the plant with a pre-defined pre-tension during production. If such a pre-defined limit for the torque to be introduced is exceeded during insertion, the screwing tool can be turned relative to the implant such that it comes to be positioned against other elements explained in the foregoing. In addition, the self-locking conical connection is preferably embodied such that the conical surface of the implant is not damaged if the pre-defined limit for the torque is exceeded and/or if the adapter rotates relative to the implant. Thus in particular the friction coefficient and/or the roughness of the conical surface of the pin of the screwing tool are inventively embodied less by a pre-specified value than the friction coefficient and/or the roughness of the conical surface and/or the interior surface of the implant. This value is in particular 10% less, advantageously 25% less, preferably 35% less. Furthermore, the value is in particular maximum 90%, advantageously 70%, preferably 35%.

In accordance with the invention, the arrangement is an implant system, including the implant, the screwing tool, and the attachment part, the pin of the screwing tool and in particular its conical exterior surface being embodied in conformance with the pin of the attachment part. In this implant system, the pin of the attachment part is preferably embodied essentially the same as the pin of the screwing tool. Moreover, the tension screw for connecting the screwing tool to the implant is advantageously embodied conforming to the tension screw provided for connecting the attachment part to the implant, in particular the complexity for production and/or provision of the aforesaid tension screw being reduced. This applies likewise for the threaded sleeve that is connected or is to be connected to the free end of the tension screw. In the inventive implant system, the implant and the screwing tool are preferably connected to one another at the plant and/or with defined and/or pre-defined pre-tension. Once the implant has been inserted into a bone, the connection is released and then the attachment part with the pin is inserted into the receiving opening of the implant and finally the self-locking conical connection between the attachment part and the implant is produced by means of the tension screw.

The invention is described in greater detail in the following using a preferred exemplary embodiment; however, this shall not constitute a limitation.

BRIEF DESCRIPTION OF THE DRAWINGS

FIG. 1 depicts a side elevation of the arrangement;

FIG. 2 depicts the arrangement in a cross-section along section line II-II in FIG. 3;

FIG. 3 depicts a cross-section of the arrangement in the section plane III-III in FIG. 1;

Figure 4:
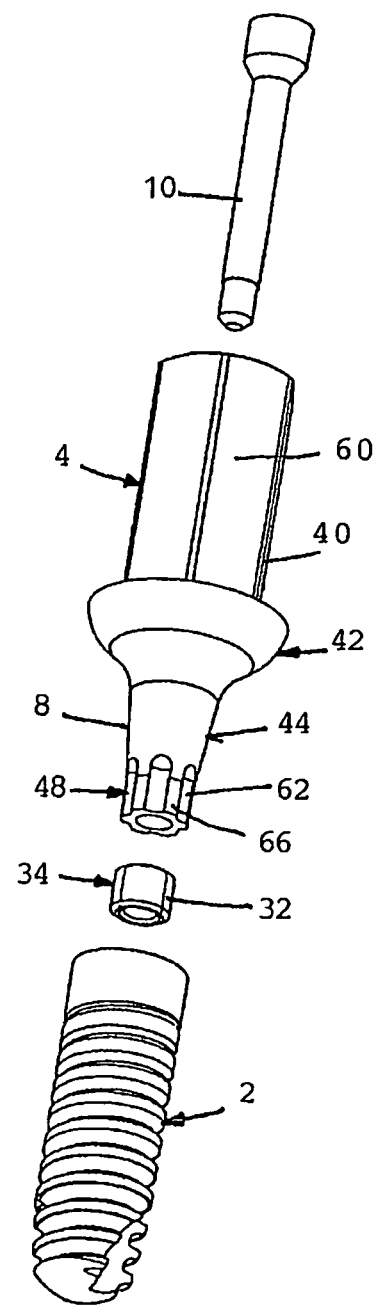
FIG. 4 is an exploded depiction of the arrangement.

In accordance with FIGS. 1 through 3, the arrangement includes the implant 2 and the screwing tool 4, the screwing tool 4 engaging in a receiving opening 6 of the implant with a pin 8. The screwing tool 4 is connected to the implant 2 by means of a tension screw 10 that is arranged in a central through-hole 12 of the screwing tool 4 essentially coaxially with the longitudinal axis 14 of the implant 2. The receiving opening 6 runs from a coronal end surface 16 of the implant 2 towards its apical end region 18 and is basically embodied as a blind hole. The implant 2 furthermore includes a male thread 20 that is preferably embodied self-cutting in the apical end region 18 and/or that has a conical thread core 22, indicated by means of the broken line, that tapers toward the apical end region 18. In the coronal end region 24 of the implant 2, the receiving opening 6 includes a conical interior surface 26 that opens toward the coronal end surface 16. Moreover, the implant 2 includes adjacent the apical end region a first indexing element 28 that engages in part in the conical interior surface 26. Provided in the end region of the receiving opening 6, which is in particular embodied as a blind hole, is a female thread 30 in which the tension screw 10 engages or is screwed in using a male thread 32. The male thread 32 is advantageously arranged on a threaded sleeve 34 that is securely connected to the interior end of the tension screw 10, in particular by welding or gluing. As can be seen from FIG. 3, the outer diameter of the threaded sleeve 34 is provided larger than the diameter of the through-hole 12 so that the screwing tool 4 is correspondingly small or embodied with a correspondingly small outer diameter. Provided in the through-hole 12 is a preferably conically embodied support surface 36 against which the screwhead 38 for the tension screw 10 is positioned. The screwing tool 4 is releasably connected to the implant with a pre-defined pre-tension by means of the tension screw 10.

The screwing tool 4 contains a head part 40, an intermediate part or expansion 42 apically adjacent or toward the implant, and the aforementioned pin 8 adjacent thereto. The screwing tool that partially engages in the recess opening 6 or its pin 8 contains a conical exterior surface 44 that conforms to and/or matches the conical interior surface 26 of the implant. The takeout angles for the conical surfaces 26 and 44 are in particular pre-defined, taking into account their friction coefficients and/or their surface quality and/or the roughness and/or the size of the surface regions adjacent to one another, such that the screwing tool 4 is fixed due to conical self-locking relative to the implant 2, a defined pre-tensioning of the screwing tool 4 to the implant 2 being provided by means of the tension screw 10. The screwing tool 4 and/or its pin 8 contains another indexing element 48 that is embodied corresponding to the first indexing element 28 of the implant 2 and engages the latter, as can be seen in FIG. 3.

The screwing tool 4 or its pin 8 is preferably embodied such that only in one partial region 50 is the conical exterior surface 44 positioned against the conical interior surface 26 of the implant 2 under pre-tension and/or in a self-locking manner. Advantageously the partial region 50 is arranged adjacent to the coronal end surface 16, while apically there is no effective support for the self-locking conical connection between the conical interior surface 26 and the pin 8. To this end in particular the takeout angle of the conical exterior surface 44 of the pin 8 can be pre-defined as larger or smaller than the takeout angle of the conical interior surface 26 by a pre-defined value. Furthermore, as indicated with the broken line 52 and greatly enlarged, the diameter of the pin 8 can be reduced apically adjacent to the partial region 50. In the framework of the invention, the partial region can alternatively be arranged adjacent to the region of the apical end or, if there are indexing elements there, can preferably be arranged occlusally adjacent thereto at the pin of the screwing tool. This is significant when, after the implant 2 has been inserted and the attachment part has been connected, the part of the conical interior surface 26 adjacent to the coronal end surface 16 of the implant 2 is used and/or provided for a tight seal with the pin of the attachment part. Thus damage to the conical interior surface of the coronal end the implant is prevented during the insertion.

The intermediate part 42 of the screwing tool 4 is preferably embodied as an expansion of the screwing tool 4 that is provided on the conical pin, a concave region 54 of the intermediate part 42 being present essentially adjacent to the conical exterior surface 44 and adjacent thereto a convex region 56. The head part 40 has a reduced exterior diameter compared to the expansion 42 and in particular its convex region 56, the expansion 42 preferably forming an annular collar with a support surface 58. The head part 40 of the screwing tool 4 contains gripping surfaces 60 for an instrument, such as e.g. a ratchet, the gripping surface 60 here being embodied for instance as a hexagon. Because of the support surface 58, the aforesaid instrument is securely guided and fixed and the instrument is prevented from slipping and even injuring the patient. Furthermore, in the framework of the invention the head part 40 is embodied for the arrangement of a temporary structure, for instance a crown, that after the implant has been inserted is joined to the head part 40 in a suitable manner by means of the screwing tool 4 and is then advantageously arranged against and/or supported on the support surface 58 of the expansion 42. Moreover, it has proved particularly useful to provide the preferably conical support surface 36 for the screwhead 38 at least approximately, usefully completely, in the expansion 42, so that the screwing tool is thick enough and thus the pre-tension force applied via the screwhead 38 by means of the tension screw 10 is introduced safely. In accordance with the invention, the pre-tension force is defined at the plant and the screwing tool 4 is releasably connected to the implant 2 by means of the tension screw 10.

The head part 40 of the screwing tool 4 in accordance with the invention is embodied as a bolt, the exterior surface of which has the at least one gripping surface for the additional tool or instrument. The head part and/or the bolt 40 exhibits a non-round exterior surface and/or a cross-section that preferably remains essentially the same across its entire length. The bolt 40 is embodied in particular as a polygon having the at least one gripping surface 60. The head part or the bolt preferably has n+1 gripping surfaces 60, n being a whole number, and/or the gripping surfaces 60 are arranged distributed uniformly around the circumference. The embodiment of the bolt 4 with a polygonal cross-section having at least three exterior surfaces is advantageous for using the additional tool or instrument, a square or, as depicted, hexagon, having proved particularly useful.

FIG. 4 is an exploded depiction of the arrangement with the implant 2, screwing tool 4, and tension screw 10 to which, after insertion into the screwing tool 4, the threaded sleeve 34, which has a male thread 32, is securely joined. The additional indexing element 48 provided adjacent to the conical exterior surface 44 of the screwing tool 4 contains axial grooves 62. As can be seen in conjunction with FIG. 3, radial projections or tappets 64 of the first indexing element 28 of the implant 2 engage in these axial grooves 62 of the screwing tool 4 or its pin 8. The indexing elements 28 and 48 are embodied like axial teeth that conform to and mesh with one another.

Figure 5:
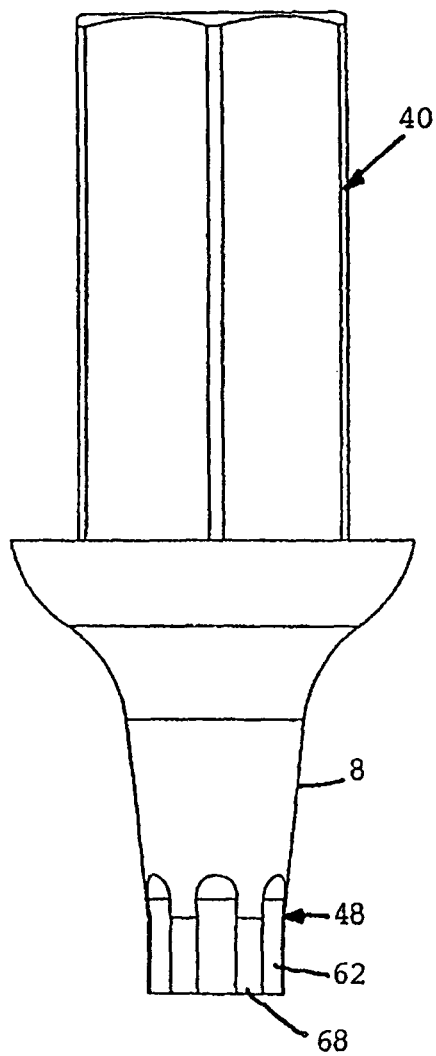
FIGS. 5, 6 depict a side elevation and perspective elevation of the screwing tool.
Figure 6:
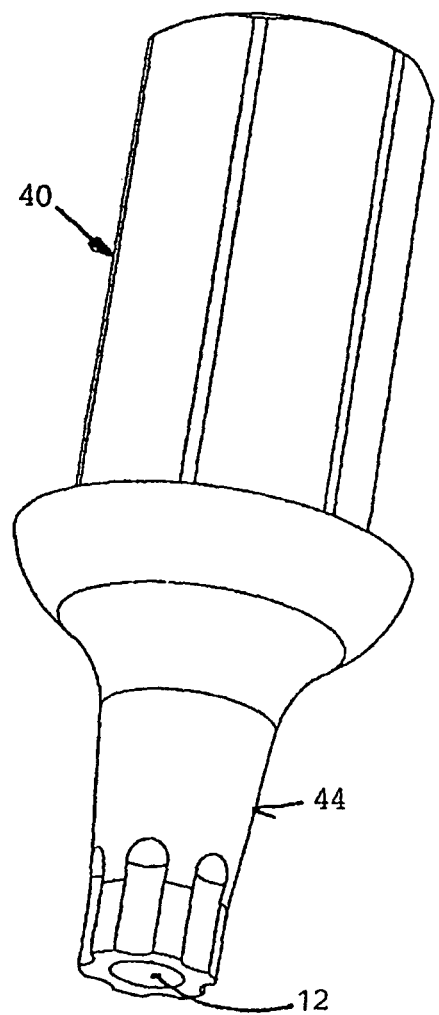

FIGS. 5 and 6 are enlarged depictions of the screwing tool 4, which contains the head part 40 having the gripping surfaces 60, the expansion 42, furthermore the pin 8 having the conical exterior surface 44, and finally the additional indexing element 48 having grooves 62 that run radially. Thus present in the circumferential direction between the grooves 62 are bars 66 that engage in corresponding grooves of the first indexing element of the implant after the pin 8 has been inserted.

Figures 7, 8:
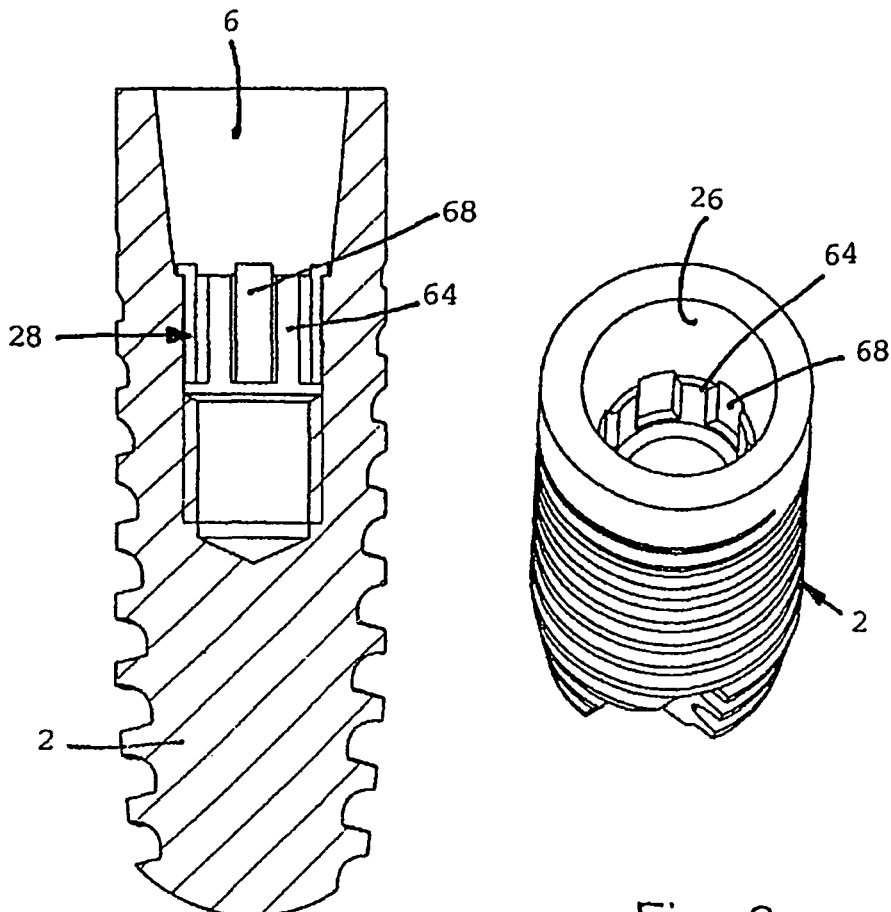
FIGS. 7, 8 depict the implant in the section plane in accordance with FIG. 2 and in a perspective elevation.

FIGS. 7 and 8 depict an axial cross-section and perspective elevation, respectively, of the implant 2 having the receiving opening 6. In its coronal end region 24 the receiving opening contains the conical interior surface 26 and furthermore apically the first indexing element 28 having the tappets 64 oriented inward radially. The aforementioned grooves 68 are disposed circumferentially between the tappets 64.

The invention claimed is:

1. An arrangement for insertion of an implant, the arrangement comprising an implant and a screwing tool, the implant having a male thread to facilitate fastening into a bone by the screwing tool, the implant having a receiving opening with at least a partially conical interior surface, whereby a pin of an attachment part can be connected to the implant after insertion of the implant by placement into the receiving opening of the implant, the screwing tool having a pin that has a conical exterior surface and engages in the receiving opening of the implant, the screwing tool being provided with a radially-expanded intermediate part positioned between the pin and a handle comprising a head part of the screwing tool, the radially-expanded intermediate part, when viewed in cross-section, increasing in diameter from the pin toward the handle and including a flat support surface forming a one-piece construction with the intermediate part of the screwing tool and lying perpendicular to a long axis of the screwing tool, the screwing tool further having a through hole and a tension screw positioned in the screw hole, the tension screw being connectable to the implant, the tension screw having a screw head in contact with an interior support surface provided in the through hole, the interior support surface being located between the pin and the flat support surface, and when viewed in cross-section, increasing in diameter in a direction extending away from the receiving opening of the implant so that a terminal portion of the interior support surface is substantially coplanar with the flat support surface, the conical exterior surface of the screwing tool being complementary to the conical interior surface of the implant and being maintained in pre-tension at least partially against the conical interior surface of the implant such that at least a pre-defined portion of the torque required for screwing in the implant can be transferred via a self-locking conical connection of the screwing tool and the implant.

2. The arrangement of claim 1, wherein the tension screw is releasably connectable with the implant by way of a male thread provided on the tension screw that screws into a female thread in the receiving opening of the implant, the male thread of the tension screw being provided on a threaded sleeve that is securely connected to the tension screw.

3. The arrangement according to claim 2, wherein the interior support surface of the though-hole of the screwing tool is conically-shaped, the conically-shaped interior support surface receiving the screw head of the tension screw, the screw head having a size and shape that is complimentary to the conically-shaped interior support surface of the through hole.

4. The arrangement of claim 1, wherein a pre-defined region of the conical exterior surface of the pin is positioned against the conical interior surface of the implant and the region is located in the vicinity of a coronal end surface of the implant.

5. The arrangement of claim 1, wherein torque is at least partially transferred via the self-locking conical connection of the conical interior surface and the conical exterior surface and torque is partially transferred via one or more of indexing elements and corresponding surfaces of the screwing tool and implant.

6. The arrangement of claim 1, wherein a limit for torque is predefined, which limit, if exceeded, is transferred in combination with a first indexing element of the implant, a second indexing element of the screwing tool, and the pin of the screwing tool.

7. The arrangement of claim 1, wherein the head part has at least one gripping surface for another instrument.

8. The arrangement of claim 7, wherein the head part exhibits one or more of: a cross-section that remains essentially the same across its entire length; is a polygon having a polygonal cross-section; and at least two gripping surfaces distributed uniformly around the circumference of the head part.

9. The arrangement of claim 7, wherein one or more portions of the intermediate part has a larger exterior diameter than the head part.

10. The arrangement of claim 1, wherein the implant has at least a first indexing element for engaging with one or more of: a second corresponding indexing element of an attachment part for determining a defined rotational angle position; a third corresponding indexing element provided on the screwing tool.

11. The arrangement of claim 1 wherein the handle of the screwing tool projects away from the implant when the screwing tool is engaged in the implant, the handle and implant being configured to lie on a common axis.

12. The arrangement of claim 1 wherein the screwing tool and the implant are connected in an arrangement in which the conical exterior surface of the pin of the screwing tool is engaged with the conical interior surface of the implant at an initial predetermined tension having a threshold value, and whereby, if the threshold value is exceeded, the screwing tool is twistable relative to the implant through an initial torque and the conical interior surface of the implant is not damaged if the threshold value for torque is exceeded and/or if the screwing tool rotates relative to the implant.

13. The arrangement of claim 12 wherein the conical exterior surface of the pin of the screwing tool is provided with a predetermined roughness value that is at least 10% less than a predetermined roughness value of the conical interior surface of the implant.

14. The arrangement of claim 12 wherein the conical exterior surface of the pin of the screwing tool is provided with a predetermined roughness value that is at least 25% less than a predetermined roughness value of the conical interior surface of the implant.

15. The arrangement of claim 12 wherein the conical exterior surface of the pin of the screwing tool is provided with a predetermined roughness value that is at least 35% less than a predetermined roughness value of the conical interior surface of the implant.

16. The arrangement of claim 1 wherein the implant further comprises a coronal end surface provided on a coronal end of the implant, the coronal end surface being dimensioned evenly across the implant.

17. The arrangement of claim 1, wherein the implant is a dental implant.

18. The arrangement of claim 1, wherein the intermediate part of the screwing tool includes a concave region that is adjacent to a conical exterior surface of the screwing tool and adjacent to a convex region, the convex region having the flat support surface on a top thereof.

19. The arrangement according to claim 1, wherein the interior support surface of the though-hole of the screwing tool is conically-shaped, the conically-shaped interior support surface receiving the screw head of the tension screw, the screw head having a size and shape that is complimentary to the conically-shaped interior support surface of the through hole.

* * * * *